US012674203B2

(12) United States Patent
Park et al.

(10) Patent No.:  US 12,674,203 B2
(45) Date of Patent:        Jul. 7, 2026

(54) SELF-PRIMING HAIRPIN-MEDIATED ISOTHERMAL AMPLIFICATION

(71) Applicant: KOREA ADVANCED INSTITUTE OF SCIENCE AND TECHNOLOGY, Daejeon (KR)

(72) Inventors: Hyun Gyu Park, Daejeon (KR); Jayeon Song, Daejeon (KR); Hyo Yong Kim, Daejeon (KR); Yujin Jung, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 895 days.

(21) Appl. No.: 17/907,188

(22) PCT Filed: Mar. 19, 2021

(86) PCT No.: PCT/KR2021/003399
§ 371 (c)(1),
(2) Date: Sep. 23, 2022

(87) PCT Pub. No.: WO2021/194169
PCT Pub. Date: Sep. 30, 2021

(65) Prior Publication Data
US 2023/0119862 A1      Apr. 20, 2023

(30) Foreign Application Priority Data
Mar. 23, 2020    (KR) ........................ 10-2020-0035028

(51) Int. Cl.
*C12Q 1/6876*        (2018.01)
*C12Q 1/686*         (2018.01)

(52) U.S. Cl.
CPC ........... *C12Q 1/6876* (2013.01); *C12Q 1/686* (2013.01); *C12Q 2525/301* (2013.01); *C12Q 2527/101* (2013.01)

(58) Field of Classification Search
CPC ............................ C12Q 1/6876; C12Q 1/686; C12Q 2525/301; C12Q 2527/101; C12Q 1/6816;
(Continued)

(56) References Cited

U.S. PATENT DOCUMENTS

2006/0068433 A1*   3/2006   Godfrey ............... C12Q 1/6851
                                                            435/6.1

FOREIGN PATENT DOCUMENTS

| KR | 1020190089944 A | 7/2019 |
|----|-----------------|--------|
| KR | 1020190092881 A | 8/2019 |
| WO | 2012058488 A9   | 5/2012 |

OTHER PUBLICATIONS

Jung et al. Ultrasensitive nucleic acid detection based on phosphorothioated hairpin-assisted isothermal amplification. Scientific Reports 2021; 11: 8399. (Year: 2021).*
(Continued)

*Primary Examiner* — Angela M. Bertagna
(74) *Attorney, Agent, or Firm* — HULTQUIST, PLLC; Steven J. Hultquist

(57) ABSTRACT
The present invention relates to a self-priming hairpin-mediated isothermal amplification (SP-HAMP) and, more specifically, to a hairpin probe having a self-priming structure, which is for detecting a target nucleic acid and can be used in the nucleic acid isothermal amplification, and to a method for detecting a target nucleic acid by using same. The SP-HAMP technique according to the present invention is convenient due to no need of a separate primer with a complicated design required in existing LAMP technology, has improved efficiency of detection compared with existing LAMP reactions, and can detect DNA as well as RNA as a
(Continued)

target nucleic acid, and therefore the technique according to the present invention can be applied in a wider variety of fields.

4 Claims, 7 Drawing Sheets

Specification includes a Sequence Listing.

(58) Field of Classification Search
CPC ................ C12Q 1/6853; C12Q 1/6848; C12Q 2525/113; C12Q 2525/125; C12Q 2525/161
See application file for complete search history.

(56) References Cited

OTHER PUBLICATIONS

Cai et al. Phosphorothioated Primers Lead to Loop-Mediated Isothermal Amplification at Low Temperatures. Analytical Chemistry 2018; 90: 8290-8294. (Year: 2018).*

Song et al. Self-Priming Hairpin-Utilized Isothermal Amplification Enabling Ultrasensitive Nucleic Acid Detection. Analytical Chemistry 2020; 92: 10350-10356 + Supporting Information. (Year: 2020).*

Jung, C., et al., "A primerless molecular diagnostic: phosphorothioated-terminal hairpin formation and self-priming extenssiion (PS-THSP)", Anal Bioanal Chem, 2016, pp. 8583-8591, vol. 408, Publisher: CrossMark.

Liu, C., et al., "2-aminopurine probe in combination with datalyzed hairpin assembly signal amplification for simple and sensitive detection of microRNA", Talanta, 2017, pp. 336-340, vol. 174, Publisher: Elsevier.

Song, J., et al., "Self-priming phosphorothiated hairpin-mediate isothermal amplification", Biosensors and Bioelectronics, 2021, p. 113051, vol. 178, Publisher: Elsevier.

Boczkowska, M., et al., "Stereodefined Phosphorothioate Analogues of DNA: Relative Thermodynamic Stability of the Model PS-DNA/DNA and PS-DNA/RNA Complexes", Biochemistry, 2002, pp. 12483-12487, vol. 41, Publisher: American Chemical Society.

Kim, H., et al., "Enzyme-free and label-free miRNA detection based on target-triggered catalytic hairpin assembly and fluoresence enhancement of DNA-silver nanoclusters", Sensors and Actuators B Chemical, 2017, https://doi.org/10.1016/j.snb.2017.12.137.

Notice of Allowance issued in Korean Patent Application No. 10-2020-0035028 on Jul. 2, 2022.

English Translation of Notice of Allowance issued in Korean Patent Application No. 10-2020-0035028 on Jul. 2, 2022.

Laplanche, L.A., et al., "Phosphorothioate-modified oligodeoxyribonucleotides, III, NMR and UV spectroscopic studies of the Rp-Rp, Sp-Sp duplexes, [d(GGSAATTCC)]2 derived from diastereomeric O-ethyl phosphorothioates", Nucleic Acids Research, 1986, pp. 9081-9093, vol. 14, No. 22, Publisher: IRL Press Limited, Oxford, England.

Mori, Y., et al., "Real-time turbidimetry of LAMP reaction for quantifying template DNA", Journal of Biochemical and Biophysical Methods, 2004, pp. 145-157, vol. 59, Publisher: Elsevier.

Notomi, T., et al., "Loop-mediated isothermal amplification of DNA", Nucleic Acids Research, 2000, e63, vol. 28, No. 12, Publisher: Oxford University Press.

Tomita, N., et al., "Loop-mediated isothermal amplification (LAMP) of gene sequences and simple visual detection of products", Nature Protocols, 2008, pp. 877-882, vol. 3, No. 5.

Van Ness, J., et al., "Isothermal reactions for the amplification of oligonucleotides", PNAS, 2003, pp. 4504-4509, vol. 100, No. 8.

* cited by examiner

FIG. 1
A
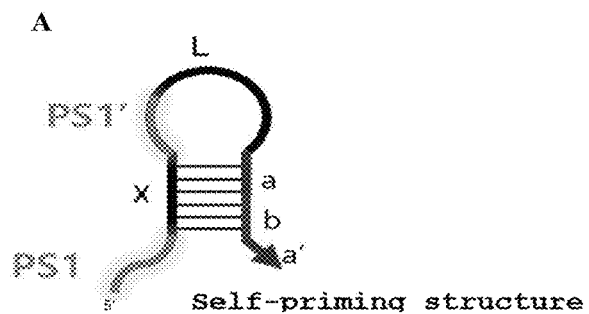
Self-priming structure
B
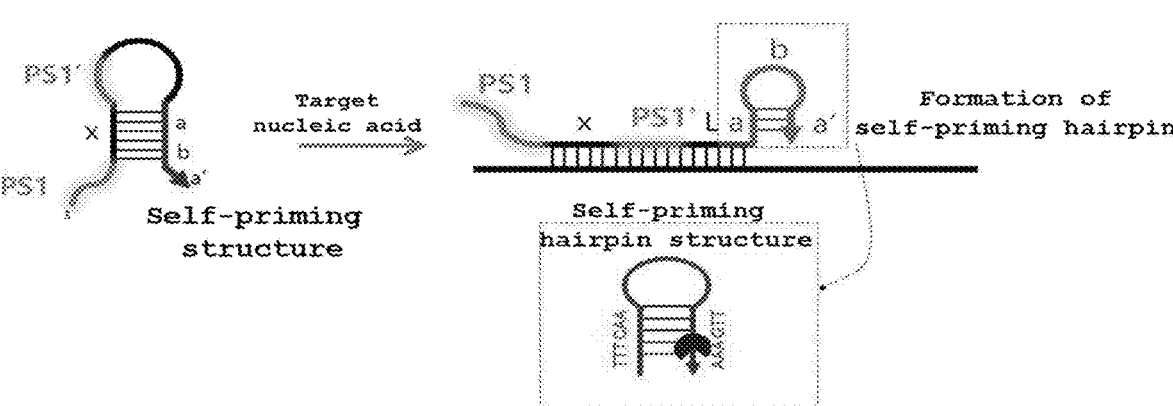

a)

b)

Curve 1 : HP_PS tail + Target + DNA Pol. (Positive)
Curve 2 : HP_PS tail + DNA Pol. (Negative)
Curve 3 : HP_DNA tail + Target + DNA Pol. (control)
Curve 4 : HP Random tail + Target + DNA Pol. (control)

√ Target : Neisseria gonorrhea (NG)

Target binding                    Extension

1. Ladder                             5. Target + HP + DNA Pol. 10 min
2. Target                             6. Target + HP + DNA Pol. 30 min
3. Hairpin probe (HP)                 7. Target + HP + DNA Pol. 60 min
4. Target + HP                        8. HP + DNA Pol. 60 min a)                                    b)

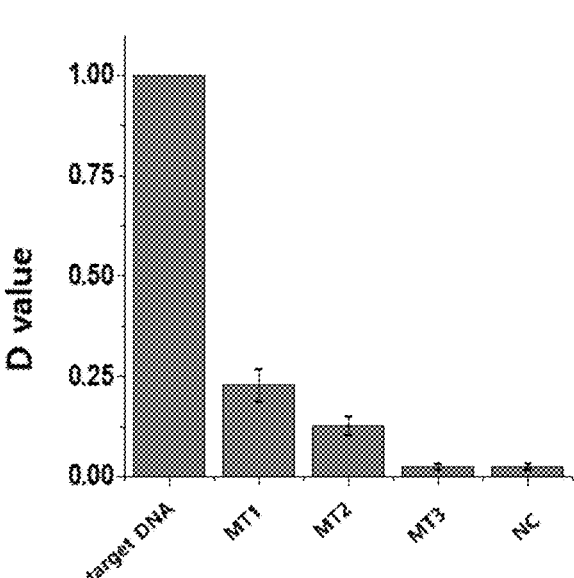

| Target DNA | AGG TCT AGG GTG CGC TCT GCT TCG GCT CTC TGC TGT TTC AAG TCG TCC AGC TCG TTC TT |
|---|---|
| MT1 | AGG TCT AGG GTC CGC TCT GCT TCG GCT CTC TGC TGT TTC AAG TCG TCC AGC TCG TTC TT |
| MT2 | AGG TCT AGG GTC GGC TCT GCT TCG GCT CTC TGC TGT TTC AAG TCG TCC AGC TCG TTC TT |
| MT3 | AGG TCT AGG GTC GCC TCT GCT TCG GCT CTC TGC TGT TTC AAG TCG TCC AGC TCG TTC TT |
| NC | AGC TTT GGC GAT TTG GTC AGG CAT AAT CGC CGA CAT TCT TTC TAC ACG GAT CCA AGT AT |

D value: the ratio between $(F_{60,0} - F_{60,X}) / (F_{60,0} - F_{60,P})$

SEQUENCE LISTING

```
<160> NUMBER OF SEQ ID NOS: 8

<210> SEQ ID NO 1
<211> LENGTH: 59
<212> TYPE: DNA
<213> ORGANISM: Artificial Sequence
<220> FEATURE:
<223> OTHER INFORMATION: Synthetic construct

<400> SEQUENCE: 1
aggtctaggg tgcgctctgc ttcggctctc tgctgtttca agtcgtccag ctcgttctt      59

<210> SEQ ID NO 2
<211> LENGTH: 82
<212> TYPE: DNA
<213> ORGANISM: Artificial Sequence
<220> FEATURE:
<223> OTHER INFORMATION: Synthetic construct

<400> SEQUENCE: 2
ttcggctctc tgcctggacg acttgaaaca gcagagagcc gaagcagagc gcaccctgct      60
gtttcaagtc gtccagttga aa                                               82

<210> SEQ ID NO 3
<211> LENGTH: 64
<212> TYPE: RNA
<213> ORGANISM: Artificial Sequence
<220> FEATURE:
<223> OTHER INFORMATION: Synthetic construct

<400> SEQUENCE: 3
gaauaaucuu ucuuucugau uguuaguucc ugcauuuaug uuucuacuuu uaucuucugc      60
uauu                                                                   64

<210> SEQ ID NO 4
<211> LENGTH: 84
<212> TYPE: DNA
<213> ORGANISM: Artificial Sequence
<220> FEATURE:
<223> OTHER INFORMATION: Synthetic construct

<400> SEQUENCE: 4
ctgattgtta gttagaaaca taaatgcagg aactaacaat cagaaagaaa gattattagt      60
tcctgcattt atgtttctaa tgca                                             84

<210> SEQ ID NO 5
<211> LENGTH: 59
<212> TYPE: DNA
<213> ORGANISM: Artificial Sequence
<220> FEATURE:
<223> OTHER INFORMATION: Synthetic construct

<400> SEQUENCE: 5
aggtctaggg tccgctctgc ttcggctctc tgctgtttca agtcgtccag ctcgttctt      59
```

-continued

```
<210> SEQ ID NO 6
<211> LENGTH: 59
<212> TYPE: DNA
<213> ORGANISM: Artificial Sequence
<220> FEATURE:
<223> OTHER INFORMATION: Synthetic construct

<400> SEQUENCE: 6
aggtctaggg tcggctctgc ttcggctctc tgctgtttca agtcgtccag ctcgttctt          59

<210> SEQ ID NO 7
<211> LENGTH: 59
<212> TYPE: DNA
<213> ORGANISM: Artificial Sequence
<220> FEATURE:
<223> OTHER INFORMATION: Synthetic construct

<400> SEQUENCE: 7
aggtctaggg tcgcctctgc ttcggctctc tgctgtttca agtcgtccag ctcgttctt          59

<210> SEQ ID NO 8
<211> LENGTH: 59
<212> TYPE: DNA
<213> ORGANISM: Artificial Sequence
<220> FEATURE:
<223> OTHER INFORMATION: Synthetic construct

<400> SEQUENCE: 8
agctttggcg atttggtcag gcataatcgc cgacattctt tctacacgga tccaagtat          59
```

SELF-PRIMING HAIRPIN-MEDIATED ISOTHERMAL AMPLIFICATION

CROSS-REFERENCE TO RELATED APPLICATIONS

This application is a U.S. national phase under 35 U.S.C. § 371 of International Patent Application No. PCT/KR2021/003399 filed Mar. 19, 2021, which in turn claims priority under 35 U.S.C. § 119 of Korean Patent Application No. 10-2020-0035028 filed Mar. 23, 2020. The disclosures of all such applications are hereby incorporated herein by reference in their respective entireties, for all purposes.

REFERENCE TO SEQUENCE LISTING

This application includes an electronically submitted sequence listing in .txt format. The .txt file contains a sequence listing entitled "650_UpdatedSeqListing_ST25.txt" created on Feb. 1, 2026 and is 2, 128 bytes in size. The sequence listing contained in this .txt file is part of the specification and is hereby incorporated by reference herein in its entirety.

TECHNICAL FIELD

The present invention relates to self-priming hairpin-mediated isothermal amplification (SP-HAMP), and more specifically, to a hairpin probe having a self-priming structure for detecting a target nucleic acid that can be used for nucleic acid isothermal amplification and a method for detecting a target nucleic acid using the same.

BACKGROUND ART

Polymerase chain reaction (hereinafter referred to as "PCR") is the most widely used method for amplification and detection of target nucleic acids. However, precise temperature control is required in order to implement a PCR reaction, and there are disadvantages in that the volume of the PCR equipment is increased and costs are increased due to the installation of a temperature controller for this purpose. Recently, as demand for the development of point-of-care testing (POCT) has increased, interest in alternative approaches capable of realizing miniaturization by overcoming the drawbacks of PCR, requiring a temperature controller is increasing.

In response to this technological trend, isothermal nucleic amplification technologies for amplifying nucleic acids at a constant temperature without conducting a temperature control process (nucleic acid sequence-based amplification (NASBA), helicase-dependent amplification (HDA), recombinase polymerase amplification (RPA), strand displacement amplification (SDA), loop-mediated isothermal amplification (LAMP), rolling-circle amplification (RCA), and exponential amplification reaction (EXPAR)) have been actively developed since the early 1990s (Van Ness et al., *Proc. Natl. Acad. Sci. U.S.A.,* 100, 4504, 2003).

Among multiple isothermal nucleic acid amplification technologies, LAMP has been considered to have has high application potential as a POCT technology because it realizes a target nucleic acid amplification efficiency of up to 10⁹ times within a short reaction time of about 1 hour. Specifically, LAMP is a technology in which a target nucleic acid is hybridized with four primers and then a dumbbell-shaped DNA product generated by the action of a DNA polymerase is amplified through hybridization with primers (Tomita, N. et al. *Nucleic Acids Res,* 28, 63, 2000; Tomita, N. et al., *Nature protocols,* 3, 877, 2008; Mori, Y. et al., *J Biochem Biophys Methods,* 59, 145, 2004). However, LAMP uses several types of primers having complicated designs, and detection efficiency is disadvantageously reduced by rapid amplification of background signals due to random hybridization between the primers.

Accordingly, the present inventors endeavored to develop an isothermal amplification method conveying higher amplification efficiency and detection efficiency than the prior art. As a result, the present inventors found that, when a hairpin probe that is modified with phosphorothioate DNA and has a self-priming structure is used, target nucleic acids can be detected with high amplification efficiency under isothermal conditions, and completed the present invention based on this finding.

DISCLOSURE

Technical Problem

It is one object of the present invention to provide a hairpin probe having a self-priming structure for detecting a target nucleic acid that can be used for nucleic acid isothermal amplification.

It is another object of the present invention to provide a method for detecting a target nucleic acid using the hairpin probe.

It is another object of the present invention to provide a composition for detecting a target nucleic acid containing the hairpin probe.

It is another object of the present invention to provide a kit for detecting a target nucleic acid containing the hairpin probe.

Technical Solution

In order to accomplish the objects, the present invention provides a hairpin probe including the following components and having a self-priming structure for detecting a target nucleic acid:

(i) a PS1 region disposed at a 5' end of the hairpin probe, the PS1 region modified with phosphorothioate DNA, the PS1 region having a sequence complementary to a PS1' region;

(ii) an X region linked to the PS1 region, the X region disposed on a stem of the hairpin probe including a sequence complementary to a target nucleic acid;

(iii) the PS1' region disposed in a loop of the hairpin probe, the PS1' region linked to the X region, the PS1' region having a sequence complementary to the target nucleic acid following the sequence complementary to the target nucleic acid of the X region, the PS1' region modified with phosphorothioate DNA;

(iv) an L region linked to the PS1' region, the L region having a sequence complementary to the target nucleic acid following the sequence complementary to the target nucleic acid of the PS1' region, the L region disposed in the loop of the hairpin probe;

(v) an a region of a self-priming hairpin, linked to the L region, the a region including a sequence complementary to a part of the X region to form a stem of the hairpin probe;

(vi) a b region of the self-priming hairpin, linked to the a region of the self-priming hairpin, the b region including a sequence complementary to a part of the X region to form the stem of the hairpin probe; and (vii) an a' region of the self-priming hairpin, disposed at a 3' end of the hairpin probe, the a' region linked to the b region of the self-priming hairpin, the a' region including a sequence complementary to the a region of the self-priming hairpin.

The present invention provides a method for detecting a target nucleic acid including: (a) reacting a composition containing a sample containing the target nucleic acid, the hairpin probe having a self-priming structure, a nucleic acid polymerase, and dNTP to obtain an intermediate product including the hairpin probe extended by the self-priming structure; and (b) analyzing the produced hairpin probe intermediate product to detect the target nucleic acid.

The present invention provides a composition for detecting a target nucleic acid containing a sample containing the target nucleic acid, the hairpin probe having a self-priming structure, a nucleic acid polymerase, and dNTP.

The present invention provides a kit for detecting a target nucleic acid containing a sample containing the target nucleic acid, the hairpin probe having a self-priming structure, a nucleic acid polymerase, and dNTP.

DESCRIPTION OF DRAWINGS

FIG. 1 in part A thereof shows the structure of the hairpin probe used in the SP-HAMP of the present invention. FIG. 1 in part B thereof schematically illustrates the formation of a self-priming hairpin through hybridization of the hairpin probe of the present invention with a target nucleic acid. The 5' end (PS1) and a loop part (PS1') of the hairpin probe are modified with phosphorothioate DNA, and include sequences complementary to each other. In addition, the stem and loop part of the hairpin probe include sequences complementary to the target nucleic acid. Accordingly, the hairpin probe is opened by the target nucleic acid and the stem (a) and the 3' end part (a') of the hairpin probe include sequences complementary to each other, so a self-priming hairpin structure is formed.

FIG. 5 shows the specificity of the SP-HAMP of the present invention and the results of an experiment performance of discriminating various base mismatch from target nucleic acids, wherein "Target DNA" has the sequence AGG TCT AGG GTG CGC TCT GCT TCG GCT CTC TGC TGT TTC AAG TCG TCC AGC TCG TTC TT (SEQ ID NO: 1), "MT1" has the sequence AGG TCT AGG GTC CGC TCT GCT TCG GCT CTC TGC TGT TTC AAG TCG TCC AGC TCG TTC TT (SEQ ID NO: 5), "MT2" has the sequence AGG TCT AGG GTC GGC TCT GCT TCG GCT CTC TGC TGT TTC AAG TCG TCC AGC TCG TTC TT (SEQ ID NO: 6), "MT3" has the sequence AGG TCT AGG GTC GCC TCT GCT TCG GCT CTC TGC TGT TTC AAG TCG TCC AGC TCG TTC TT (SEQ ID NO: 7), and "NC" has the sequence AGC TTT GGC GAT TTG GTC AGG CAT AAT CGC CGA CAT TCT TTC TAC ACG GAT CCA AGT AT (SEQ ID NO: 8).

BEST MODE

Figure 2:
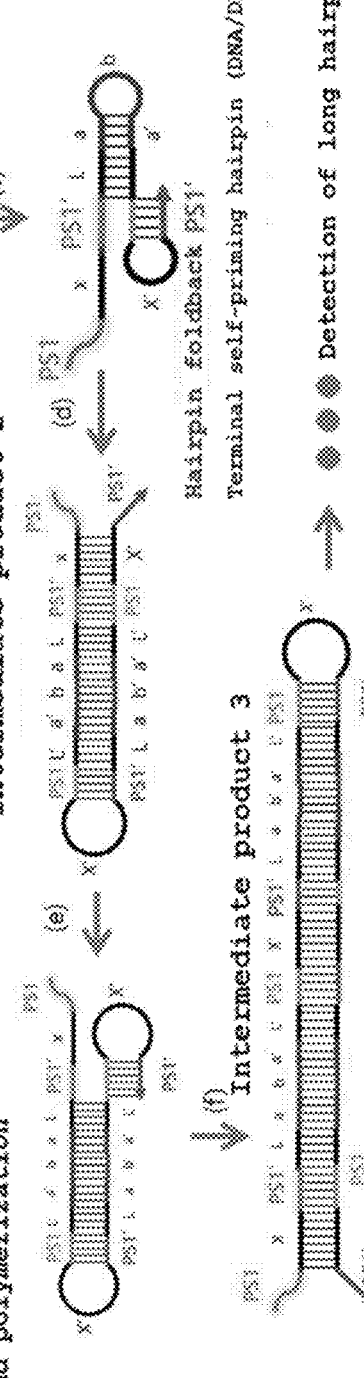
FIG. 2 is a schematic diagram illustrating a reaction involving SP-HAMP according to the present invention. More specifically, (a) shows allowing the hairpin probe to be opened through hybridization with a target nucleic acid, (b) shows production of intermediate product 1 through polymerization of the hairpin probe, (c) shows production of a terminal self-priming hairpin construct by forming a DNA/DNA bond stronger than a weak bond between phosphorothioate DNA and normal DNA, (d) shows production of intermediate product 2 through polymerization using a DNA polymerase in the terminal self-priming hairpin, (e) shows a terminal self-priming hairpin construct in the intermediate product 2 produced in (d), and (f) shows production of intermediate product 3 through polymerization of the terminal self-priming hairpin. The terminal self-priming hairpin is constantly formed from the intermediate product yielded as a result of polymerization and polymerization is induced.

Unless defined otherwise, all technical and scientific terms used herein have the same meanings as appreciated by those skilled in the field to which the present invention pertains. In general, the nomenclature used herein is well-known in the art and is ordinarily used.

In the present invention, in order to develop a POCT (point-of-care testing) strategy capable of detecting target nucleic acid ins the field and of establishing a competitive market position, self-priming hairpin-mediated isothermal amplification (SP-HAMP) utilizing a hairpin probe that is modified with phosphorothioate DNA and has a self-priming structure was developed by overcoming the problem with the conventional nucleic acid isothermal amplification method, LAMP, in that multiple primers having a complicated design are required.

More specifically, in the present invention, the hairpin probe modified with phosphorothioate DNA and having a self-priming structure forms a self-priming hairpin structure through a target nucleic acid recognition reaction and forms a long hairpin polymer product through the action of a DNA polymerase. This simplifies a nucleic acid amplification reaction and affords a novel isothermal nucleic acid amplification method that overcomes the drawback of LAMP in that multiple primers having a complicated design are required, and has excellent amplification efficiency using only a single hairpin probe.

Therefore, in one aspect, the present invention provides a hairpin probe including the following components and having a self-priming structure for detecting target nucleic acids:

(i) a PS1 region disposed at a 5' end of the hairpin probe, the PS1 region modified with phosphorothioate DNA, the PS1 region having a sequence complementary to a PS1' region;

(ii) an X region linked to the PS1 region, the X region disposed on a stem of the hairpin probe including a sequence complementary to a target nucleic acid;

(iii) the PS1' region disposed in a loop of the hairpin probe, the PS1' region linked to the X region, the PS1' region having a sequence complementary to the target nucleic acid following the sequence complementary to the target nucleic acid of the X region, the PS1' region modified with phosphorothioate DNA;

(iv) an L region linked to the PS1' region, the L region having a sequence complementary to the target nucleic acid following the sequence complementary to the target nucleic acid of the PS1' region, the L region disposed in the loop of the hairpin probe;

(v) an a region of a self-priming hairpin, linked to the L region, the a region including a sequence complementary to a part of the X region to form a stem of the hairpin probe;

(vi) a b region of the self-priming hairpin, linked to the a region of the self-priming hairpin, the b region including a sequence complementary to a part of the X region to form the stem of the hairpin probe; and (vii) an a' region of the self-priming hairpin, disposed at a 3' end of the hairpin probe, the a' region linked to the b region of the self-priming hairpin, the a' region including a sequence complementary to the a region of the self-priming hairpin.

The structure of the hairpin probe having the self-priming structure of the present invention is shown in FIG. 1. The 5' end (PS1) and a loop part (PS1') of the hairpin probe of the present invention are modified with phosphorothioate DNA and include sequences complementary to each other. In addition, the stem and loop part of the hairpin probe include a sequence complementary to the target nucleic acid. Accordingly, the hairpin probe is opened by the target nucleic acid, and the stem (a) and the 3' end (a') of the hairpin probe include complementary sequences, thus forming a self-priming hairpin structure.

In the present invention, when the DNA modified with phosphorothioate DNA forms a double strand by base pairing (i.e., when only a single strand of the double strand is modified with phosphorothioate), it forms a weaker bond than a normal DNA base pair bond. Therefore, when another normal DNA strand complementary thereto is present, the weak bond is broken and a strong bond with the normal DNA strand is formed.

The phosphorothioate DNA alleviates the base-stacking binding force in the double helix structure, thereby lowering the melting temperature ($T_m$) between phosphorothioate DNA and DNA (Boczkowska, M. et al., *Biochemistry*, 41, 12483, 2002) (LaPlanche, L. A. et al., 14, *Nucleic acid Res,* 9081, 1986).

Figures 3, 4:
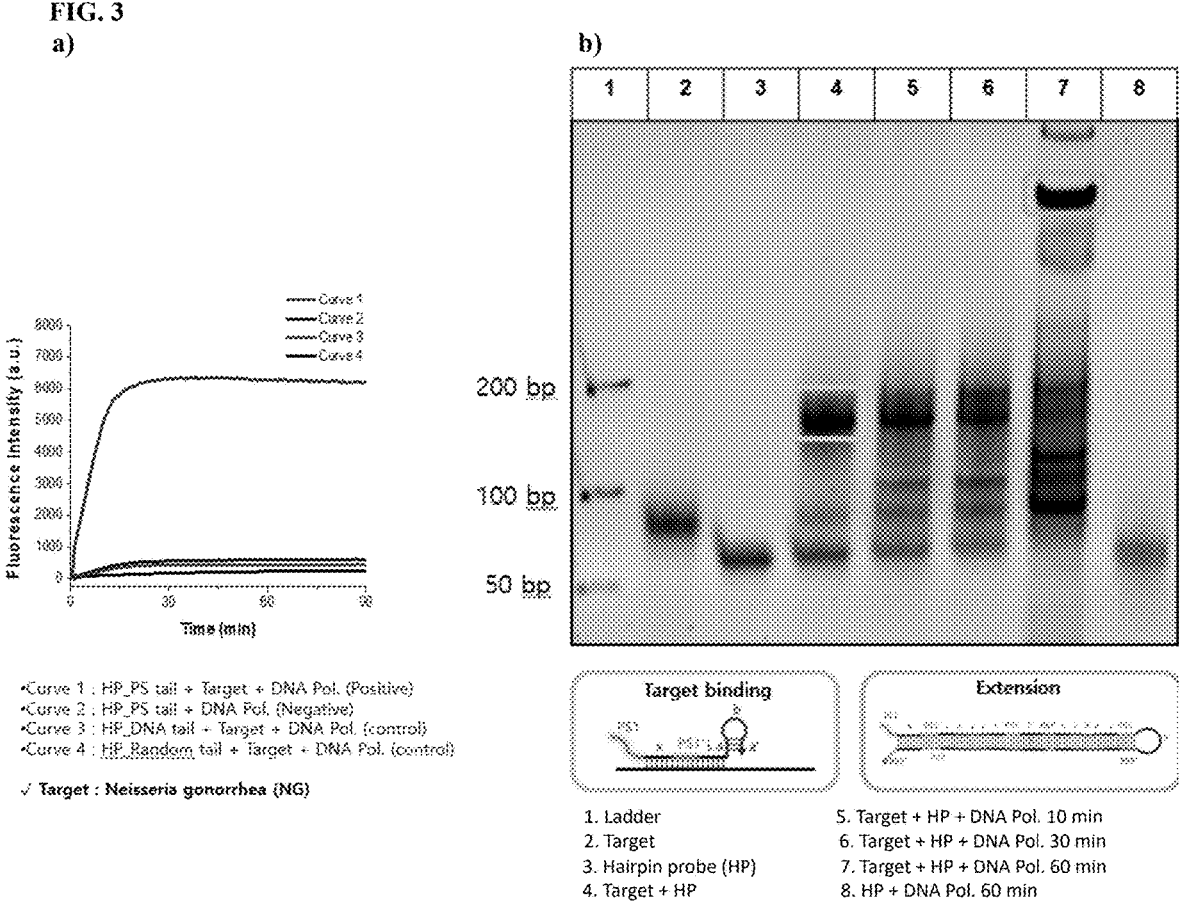
FIG. 3 shows the result of an experiment to determine the effectiveness of SP-HAMP through fluorescence measurement and electrophoresis. More specifically, FIG. 3 in part a) thereof shows the result of an experiment to confirm whether or not a fluorescence signal is generated under various conditions (1: hairpin probe modified with phosphorothioate DNA and having self-priming structure+target nucleic acid+DNA polymerase, 2: hairpin probe modified with phosphorothioate DNA and having self-priming structure+target nucleic acid+DNA polymerase, 3: hairpin probe having 5' end and self-priming structure, and including normal DNA instead of phosphorothioate DNA+target nucleic acid+DNA polymerase, 4: hairpin probe having 5' end and self-priming structure, and including DNA having random sequence instead of phosphorothioate DNA+target nucleic acid+DNA polymerase). In addition, FIG. 3 in part b) thereof shows the results of an experiment confirming the amplification products through electrophoresis under various conditions (1: ultralow range ladder, 2: target nucleic acid, 3: hairpin probe, 4: target nucleic acid+hairpin probe, 5: target nucleic acid+hairpin probe+DNA polymerase (10 min), 6: target nucleic acid+hairpin probe+DNA polymerase (30 min), 7: target nucleic acid+hairpin probe+DNA polymerase (1 hour), 8: hairpin probe+DNA polymerase (1 hour)).
FIG. 4 in the graphs a) and b) thereof shows the results of an experiment on the target nucleic acid detection sensitivity of the SP-HAMP of the present invention ($F_{60}$=F/$F_0$=fluorescence signal value of sample containing nucleic acid after 60 minutes/fluorescence signal value of sample containing no nucleic acid after 60 minutes).

In the present invention, when the target nucleic acid is present, an intermediate product is produced by extension of the hairpin probe by the self-priming hairpin, and the intermediate product is obtained in accordance with the following process (see FIG. 2):

(a) hybridizing the X, PS1' and L regions of the hairpin probe with a target nucleic acid and opening the hairpin probe to allow the self-priming structure (a' region) on the stem to form a self-priming hairpin (a of FIG. 2);

(b) reacting the self-priming hairpin (a') produced in (a) above with a DNA polymerase to form an intermediate product 1 in which a predetermined portion of the stem and an end of the stem form a bond (PS1'-PS1) between normal DNA and phosphorothioate DNA (b of FIG. 2);

(c) breaking the weak bond between phosphorothioate DNA (PS1') and normal DNA (PS1) in the intermediate product 1 by the strong bond (PS1'-PS1) between phosphorothioate DNA and phosphorothioate DNA, to cause the hairpin to be folded back and thereby form a terminal self-priming hairpin structure (c of FIG. 3);

(d) polymerizing the terminal self-priming hairpin produced in (c) by reaction with a DNA polymerase to produce a hairpin probe intermediate product 2 having an extended length (d of FIG. 2);

(e) secondarily allowing the hairpin to be folded back in the hairpin probe intermediate product 2 produced in (d) to form a terminal self-priming hairpin again (e of FIG. 2); and (f) repeatedly and continuously performing polymerization to continuously form an intermediate product (f of FIG. 2).

In one aspect of the present invention, the limit of detection (LOD) of the SP-HAMP was determined. The result showed that the target nucleic acid detection limit was 11.5 zM, which indicates that the SP-HAMP of the present invention exhibits performance comparable to that of conventional LAMP.

In another aspect of the present invention, various lengths and types of DNA (synthetic 59mer DNA, 221mer single-stranded DNA, 221mer double-stranded DNA, 548mer single-stranded DNA, and 548mer double-stranded DNA) are prepared, a hairpin probe was produced using the same as a target nucleic acid, and whether or not a long nucleic acid could be detected when SP-HAMP reaction was performed was determined.

In another aspect of the present invention, it was determined that the target nucleic acid can be effectively detected at 45 to 65° C. when the SP-HAMP reaction is performed at various temperatures.

In one aspect of the present invention, a Vent exo(−) polymerase was used as the DNA polymerase, but the system could be driven even within a reaction temperature (25° C. to 70° C.) having a wide range of solubility using various DNA polymerases. At this time, whether or not the shape of the corresponding hairpin probe changes within the temperature range is observed. If the shape is not changed, the hairpin probe is applicable. In addition to the Vent exo(−) polymerase, Bst 2.0 DNA polymerase, Bst 2.0 WarmStart™ DNA Polymerase, Klenow Fragment (3'→5' exo−), and the like may be used, but the present invention is not limited thereto.

In the present invention, it is expected that when the length of stem portions (x, a, b, and a') of the hairpin probe, DNA bases (A, T, C, and G), and chemical modification are optimized, system efficiency can be further increased.

In another embodiment of the present invention, it was found that, when the SP-HAMP reaction was performed using RNA as a target nucleic acid, the hairpin probe intermediate product was produced only in a sample containing RNA, and the SP-HAMP according to the present invention is capable of detecting RNA.

In another aspect, the present invention provides a method of detecting a target nucleic acid including (a) reacting a composition containing a sample containing the target nucleic acid, the hairpin probe having a self-priming structure, a nucleic acid polymerase, and dNTP, to produce an intermediate product including the hairpin probe extended by the self-priming structure, and (b) analyzing the produced hairpin probe intermediate product to detect the target nucleic acid.

When the target nucleic acid is present in the present invention, as described above, a hairpin probe intermediate product having a long chain is produced by extension of the self-priming hairpin probe, and the target nucleic acid can be detected by analyzing the hairpin probe intermediate product.

Whether or not the hairpin probe intermediate product having a size larger than the original hairpin probe is formed can be detected through electrophoresis or using a fluorescent dye or other method capable of detecting dsDNA.

In the present invention, the target nucleic acid may be DNA or RNA.

In one embodiment of the present invention, SYBR Green I was used as the fluorescent dye capable of detecting dsDNA, but the present invention is not limited thereto.

The SP-HAMP of the present invention is capable of successfully distinguishing non-specific sequences other than the target nucleic acid as well as one to three base mismatches and exhibits excellent specificity.

In another aspect, the present invention provides a composition for detecting a target nucleic acid containing a sample containing the target nucleic acid, the hairpin probe having a self-priming structure, a nucleic acid polymerase, and dNTP.

In another aspect, the present invention provides a kit for detecting a target nucleic acid containing a sample containing the target nucleic acid, the hairpin probe having a self-priming structure, a nucleic acid polymerase, and dNTP.

Hereinafter, the present invention will be described in more detail with reference to the following examples. However, it will be obvious to those skilled in the art that the following examples are provided only for illustration of the present invention and should not be construed as limiting the scope of the present invention.

Example 1: Establishment of Reaction Conditions of SP-HAMP

The reaction solution for the self-priming hairpin-mediated isothermal amplification (SP-HAMP) is prepared as follows. The reaction solution for SP-HAMP (final amount of 20 μL) was prepared by adding 0.4 μL of dNTPs (10 mM each), 1 μL of hairpin probe (1 μM), and 2 μL of target nucleic acids at various concentrations to a reaction buffer. The reaction buffer prepared herein contained 20 mM Tris-HCl (pH 8.8), 10 mM KCl, 10 mM $(NH_4)_2SO_4$, 2 mM $MgSO_4$, and 0.1% TritonX-100. 0.5 μL of a vent (exo-) DNA polymerase (2 unit/μL, New England Biolabs Inc. (Beverly, MA, USA)) was added to the prepared reaction solution, fluorescence intensity generated from SYBR Green I was measured at 55° C. at intervals of 30 seconds and the amount of double-stranded DNA (hairpin probe intermediate product) that was finally produced was analyzed.

TABLE 1

| | Sequence information (5'→3') |
|---|---|
| Target nucleic acid (SEQ ID NO: 1) | AGG TCT AGG GTG CGC TCT GCT TCG GCT CTC TGC TGT TTC AAG TCG TCC AGC TCG TTC TT |
| Hairpin (SEQ ID NO: 2) | TTC GGC TCT CTG CCT GGA CGA CTT GAA ACA GCA GAG AGC CGA AGC A GA GCG CAC CCT GCT GTT TCA AGT CGT CCA GTT GAA A |

Example 2. Validation of Effectiveness of SP-HAMP

The experiment to determine the effectiveness of the SP-HAMP of the present invention was conducted under the same reaction conditions as in Example 1, that is, using the same target nucleic acids and hairpin probes.

The experiment was performed under various conditions as shown in Table 2.

TABLE 2

| Experimental group | Added ingredients | Remarks |
|---|---|---|
| 1 | Hairpin probe modified with phosphorothioate DNA and having self-priming structure + target nucleic acid + DNA polymerase | SP-HAMP |
| 2 | Hairpin probe modified with phosphorothioate DNA and having self-priming structure + DNA polymerase | Target nucleic acid X |
| 3 | Hairpin probe having 5' end and self-priming structure, and including normal DNA instead of phosphorothioate DNA + target nucleic acid + DNA polymerase | PS-modified X |
| 4 | Hairpin probe having 5' end and self-priming structure, and including DNA having random sequence instead of phosphorothioate DNA + primer target nucleic acid + DNA polymerase | Random sequence |

As a result, it can be seen from a) of FIG. 3 that a very high fluorescence signal was generated under the reaction conditions including all of the target nucleic acid, the hairpin probe, and the DNA polymerase (Curve 1).

In addition, the generation of other intermediates during the reaction time was detected through electrophoresis.

TABLE 3

| Experimental group | Added ingredients | Reaction time |
|---|---|---|
| 1 | Hairpin probe modified with phosphorothioate DNA and having self-priming structure + target nucleic acid + DNA polymerase | 10 minutes |
| 2 | Hairpin probe modified with phosphorothioate DNA and having self-priming structure + target nucleic acid + DNA polymerase | 30 minutes |
| 3 | Hairpin probe modified with phosphorothioate DNA and having self-priming structure + target nucleic acid + DNA polymerase | 60 minutes |
| Control group | Hairpin probe modified with phosphorothioate DNA and having self-priming structure + DNA polymerase | 60 minutes |

As a result, as can be seen from b) of FIG. 3, a large amount of double-stranded DNA product was produced as time elapsed under reaction conditions. Meanwhile, no amplification product was identified in the absence of a target nucleic acid.

Example 3. Verification of Sensitivity of Isothermal Nucleic Acid Amplification Using DNA Polymerase Activity The experiment to determine the sensitivity of the SP-HAMP of the present invention was conducted using the reaction conditions described in Example 1. Assay samples (20 μL) containing target nucleic acids at various concentrations (1 aM~1 nM) were prepared and then SP-HAMP was performed.

As a result, as can be seen from FIG. 4, the limit of detection (LOD) of the SP-HAMP was 11.5 zM. This experimental result showed that the SP-HAMP proposed in the present invention has performance comparable to that of conventional LAMP.

Example 4. Verification of Specificity for Detection of Target Nucleic Acids by SP-HAMP The target nucleic acid detection specificity of the SP-HAMP of the present invention was determined using the reaction conditions used in Example 1. The reaction was performed using a sample (see FIG. 5) containing a random sequence of a nucleic acid other than the target nucleic acid.

As a result, as can be seen from FIG. 5, the SP-HAMP of the present invention is capable of successfully distinguishing non-specific sequences other than the target nucleic acid as well as one to three base mismatches (FIG. 5.) The experimental result showed that the SP-HAMP proposed in the present invention has excellent specificity.

Here, the D value is a parameter indicating the ability to distinguish a mismatched base from a target nucleic acid, and may be defined in accordance with the following Equation:

$$D \text{ value} = (F_{60,X} - F_{60,0})/(F_{60,P} - F_{60,0})$$

($F_{60,X}$: fluorescence signal value after 60 minutes for samples containing various base-mismatched nucleic acids; $F_{60,0}$: fluorescence signal value after 60 minutes for sample containing no target nucleic acid; $F_{60,P}$: fluorescence signal value after 60 minutes for sample containing target nucleic acid)

Example 5. Validation of Effectiveness of SP-HAMP at Various Reaction Temperatures Only the reaction temperature was varied from 37° C. to 65° C. using vent (exo-) DNA polymerase (2 unit/μL, New England Biolabs Inc. (Beverly, MA, USA)) under the reaction conditions described in Example 1. Thus, the effectiveness of the SP-HAMP of the present invention was determined for each temperature.

Figure 6:
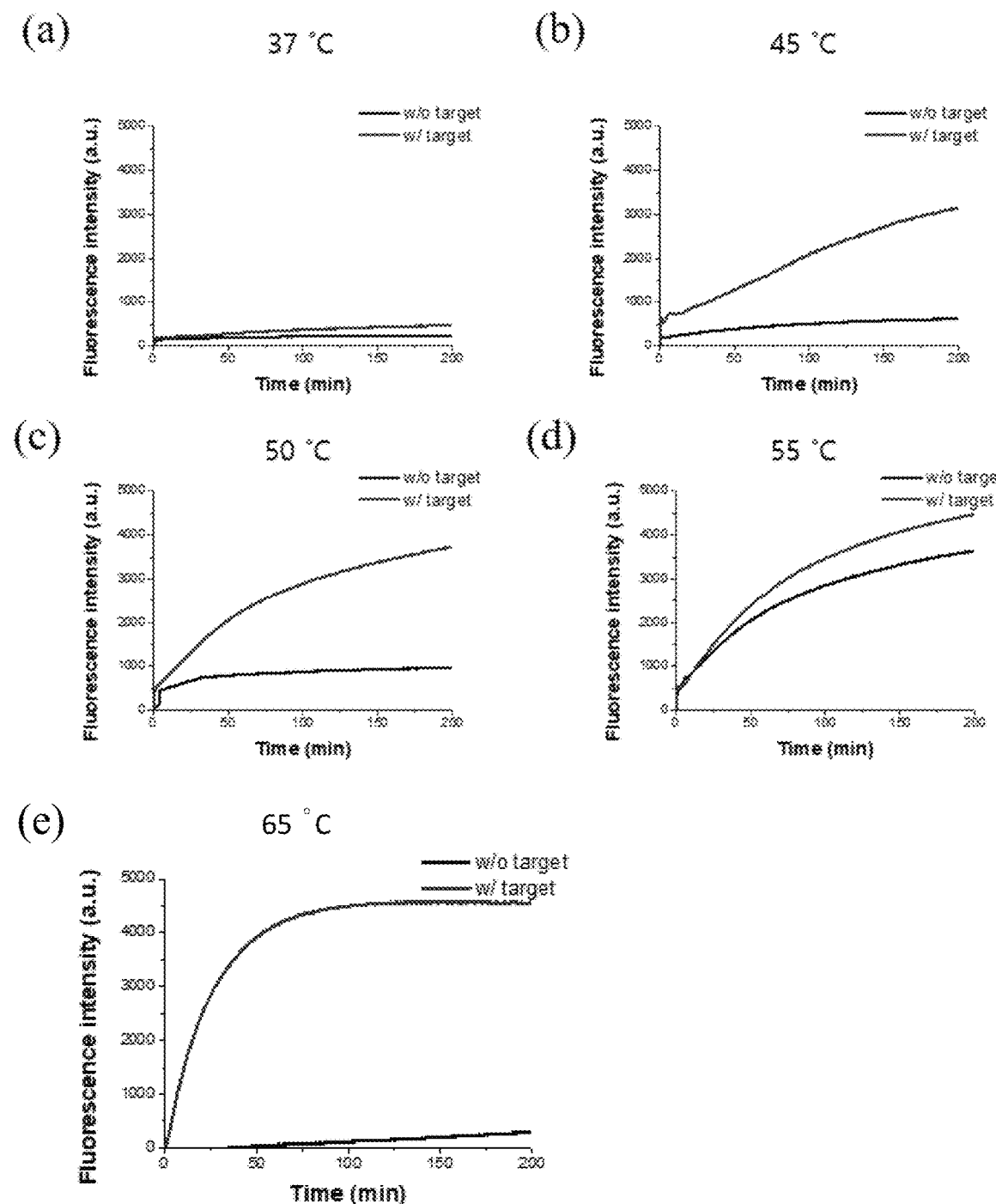
FIG. 6 shows the results of confirming the effectiveness of the SP-HAMP of the present invention at various temperatures: (a) 37° C.; (b) 45° C.; (c) 50° C.; (d) 55° C.; and (e) 65° C.

As a result, as can be seen from FIG. 6, although there was a difference in reaction efficiency at 45 to 65° C., detection of the target nucleic acid was possible.

Example 6. Verification of Practical Applicability of SP-HAMP

In order to verify the practical applicability of the SP-HAMP of the present invention using the reaction conditions described in Example 1, nucleic acid DNA having a long single-stranded structure or a double-stranded structure was obtained using PCR and asymmetric PCR and then the effectiveness of SP-HAMP was determined.

Various lengths and types of DNA (synthetic 59mer DNA, 221mer single-stranded DNA, 221mer double-stranded DNA, 548mer single-stranded DNA, and 548mer double-stranded DNA) were prepared, a hairpin probe for the target nucleic acid was produced using the same as a target nucleic acid, and the reaction was performed.

Figure 7:
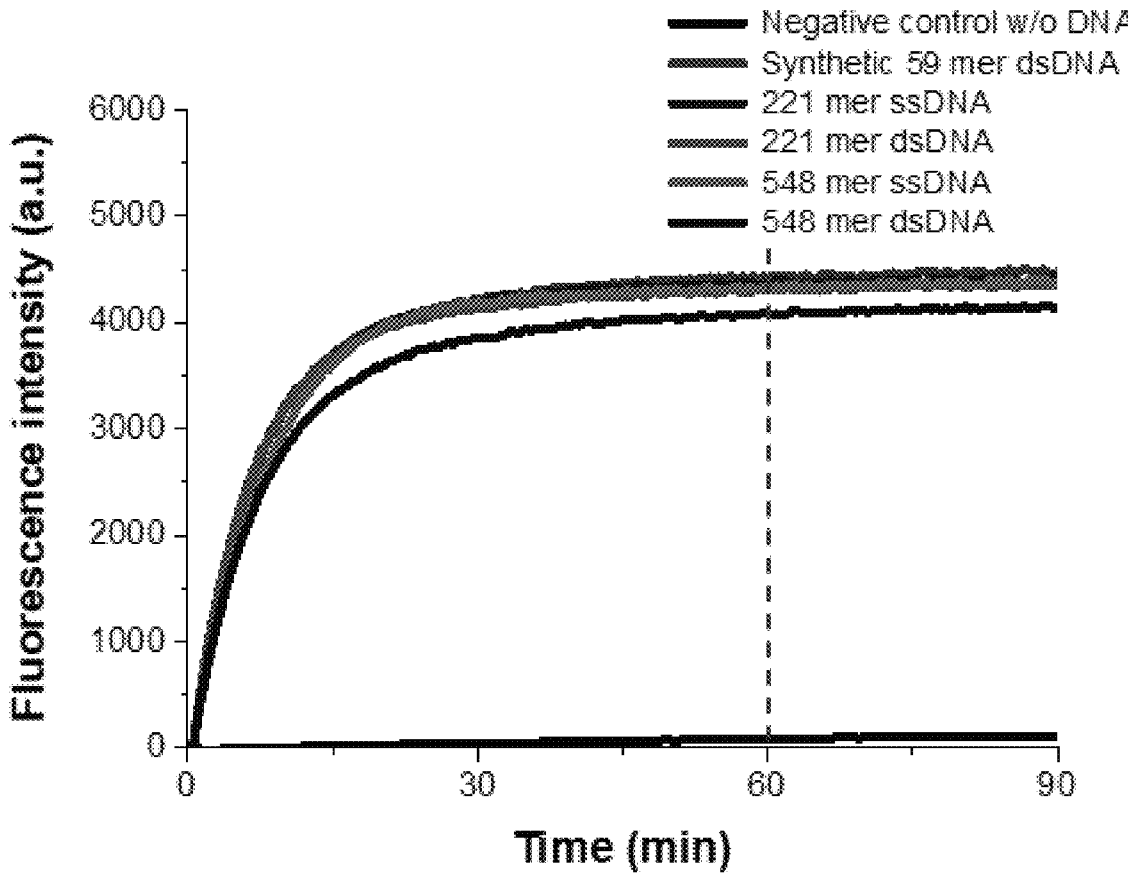
FIG. 7 demonstrates the practical applicability of the SP-HAMP of the present invention. The results of measurement of fluorescence signals using samples of long single-stranded and double-stranded nucleic acids obtained through PCR and asymmetric PCR showed that the obtained signal value was the same as that obtained for the short nucleic acid sample.

As a result, as can be seen from FIG. 7, the SP-HAMP according to the present invention can detect long nucleic acids.

Example 7. Verification of Applicability of SP-HAMP to RNA Target

Whether or not the SP-HAMP according to the present invention is capable of detecting RNA as a target nucleic acid of was determined.

As the target nucleic acid, cytochrome c oxidase subunit I mRNA of *Brachionus rotundiformis* (BR) was selected, a hairpin probe was designed, and SP-HAMP amplification was performed.

Figure 8:
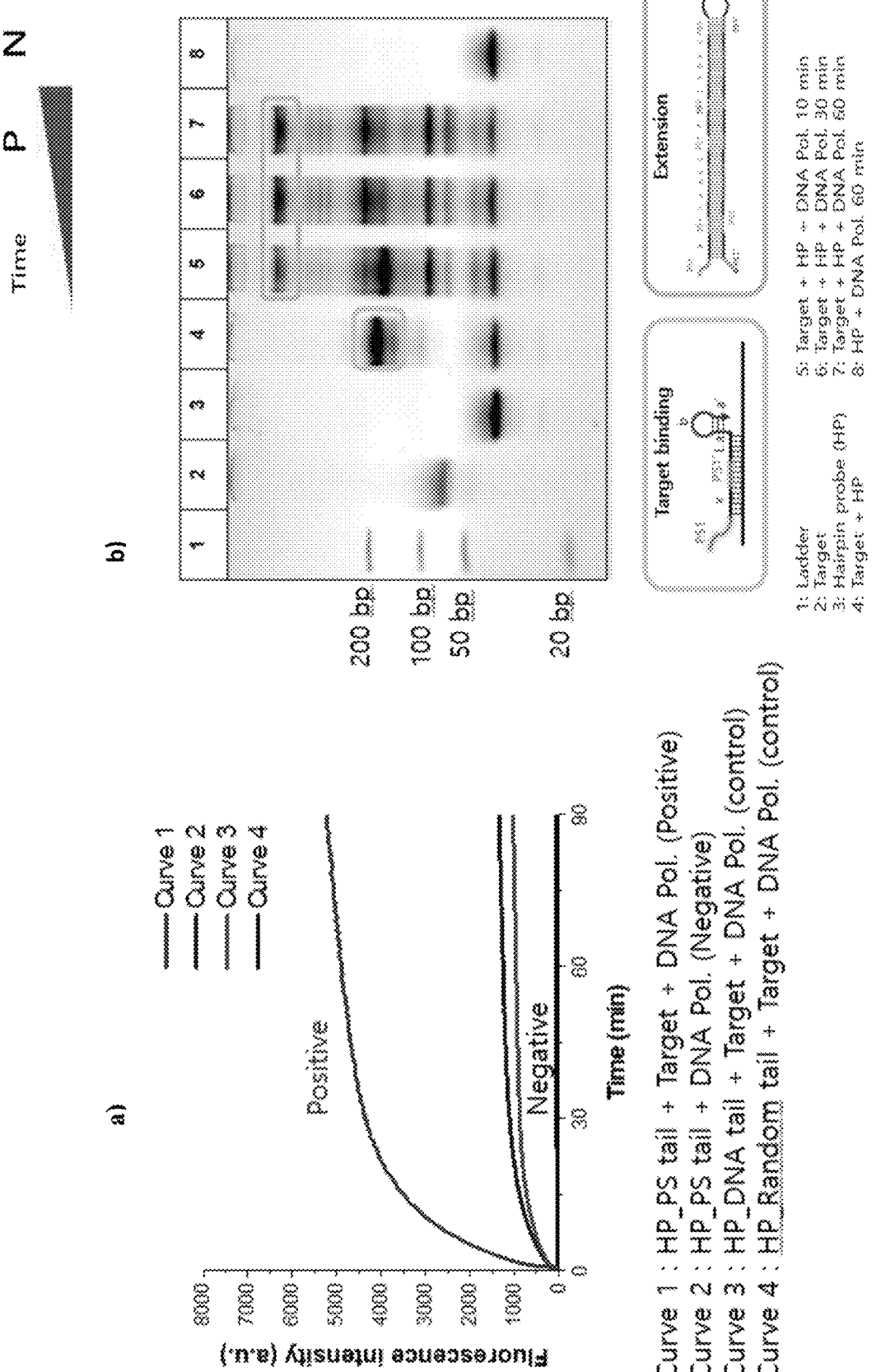
FIG. 8 shows the applicability of the SP-HAMP of the present invention to an RNA target. The result of an experiment performed after replacing the target nucleic acid with single-stranded RNA rather than DNA showed in a) that the fluorescence signal was increased only in the sample containing RNA and in b) that the formation of amplification products as time elapsed was detected again by electrophoresis.

As a result, as can be seen from FIG. 8, the fluorescence signal was increased only in the sample containing RNA, and the formation of amplification product over time was detected through electrophoresis. Therefore, it can be seen that the SP-HAMP according to the present invention is capable of detecting RNA.

TABLE 4

| | Sequence Information (5'→3') |
|---|---|
| Target nucleic acid (RNA) (SEQ ID NO: 3) | GAA UAA UCU UUC UUU CUG AUU GUU AGU UCC UGC AUU UAU GUU UCU ACU UUU AUC UUC UGC UAU U |
| Hairpin (SEQ ID NO: 4) | CTG ATT GTT AGT TAG AAA CAT AAA TGC AGG AAC TAA CAA TCA GAA A GA AAG ATT ATT AGT TCC TGC ATT TAT GTT TCT AAT GCA |

INDUSTRIAL AVAILABILITY

The SP-HAMP according to the present invention is simple because it does not require a separate primer having a complicated design, which is required for conventional LAMP, has detection efficiency superior to that of a conventional LAMP reaction, and can detect not only DNA but also RNA as a target nucleic acid, and thus is applicable to a wider range of fields.

Although specific configurations of the present invention have been described in detail, those skilled in the art will appreciate that the preferred embodiments in the description are merely given for illustrative purposes and should not be construed as limiting the scope of the present invention.

Therefore, the substantial scope of the present invention is defined by the accompanying claims and equivalents thereto.

SEQUENCE LISTING FREE TEXT

An electronic file is attached.

---

The invention claimed is:

1. A hairpin probe comprising the following components and having a self-priming structure for detecting target nucleic acids:

(i) a PS1 region disposed at a 5' end of the hairpin probe, the PS1 region modified with phosphorothioate DNA, the PS1 region having a sequence complementary to a PS1' region:

(ii) an X region linked to the PS1 region, the X region disposed on a stem of the hairpin probe including a sequence complementary to a target nucleic acid;

(iii) the PS1' region disposed in a loop of the hairpin probe, the PS1' region linked to the X region, the PS1' region having a sequence complementary to the target nucleic acid following the sequence complementary to the target nucleic acid of the X region, the PS1' region modified with phosphorothioate DNA;

(iv) an L region linked to the PS1' region, the L region having a sequence complementary to the target nucleic acid following the sequence complementary to the target nucleic acid of the PS1' region, the L region disposed in the loop of the hairpin probe;

(v) an a region of a self-priming hairpin, linked to the L region, the a region including a sequence complementary to a part of the X region to form a stem of the hairpin probe;

(vi) a b region of the self-priming hairpin, linked to the a region of the self-priming hairpin, the b region including a sequence complementary to a part of the X region to form the stem of the hairpin probe; and (vii) an a' region of the self-priming hairpin, disposed at a 3' end of the hairpin probe, the a' region linked to the b region of the self-priming hairpin, the a' region including a sequence complementary to the a region of the self-priming hairpin.

2. A method for detecting a target nucleic acid comprising:

(a) reacting a composition containing a sample containing the target nucleic acid, the hairpin probe having the self-priming structure according to claim 1, a nucleic acid polymerase, and dNTPs to obtain an intermediate product including the hairpin probe extended by the self-priming structure; and (b) analyzing the produced hairpin probe intermediate product to detect the target nucleic acid.

3. A composition for detecting a target nucleic acid comprising:

a sample containing the target nucleic acid;

the hairpin probe having the self-priming structure according to claim 1;

a nucleic acid polymerase; and dNTPs.

4. A kit for detecting a target nucleic acid comprising:

the hairpin probe having the self-priming structure according to claim 1.

* * * * *